US012741934B2

(12) United States Patent
Karsten et al.

(10) Patent No.: US 12,741,934 B2
(45) Date of Patent: Sep. 22, 2026

(54) METHOD FOR THE PREPARATION OF DIARYLMETHANE DYES AND TRIARYLMETHANE DYES INCLUDING ISOSULFAN BLUE

(71) Applicant: NJ Bio, Inc., Princeton, NJ (US)

(72) Inventors: Bram Pieter Karsten, Princeton, NJ (US); Stephen David Kozuch, Princeton, NJ (US); Nareshkumar Jain, Princeton, NJ (US)

(73) Assignee: NJ BIO, INC., Princeton, NJ (US)

( * ) Notice: Subject to any disclaimer, the term of this patent is extended or adjusted under 35 U.S.C. 154(b) by 948 days.

(21) Appl. No.: 17/624,882

(22) PCT Filed: Jul. 13, 2020

(86) PCT No.: PCT/US2020/041749
§ 371 (c)(1),
(2) Date: Jan. 5, 2022

(87) PCT Pub. No.: WO2021/011440
PCT Pub. Date: Jan. 21, 2021

(65) Prior Publication Data

US 2022/0289671 A1 Sep. 15, 2022

Related U.S. Application Data

(60) Provisional application No. 62/873,380, filed on Jul. 12, 2019.

(51) Int. Cl.
*C07C 303/06* (2006.01)
*C07C 303/22* (2006.01)
*C09B 11/18* (2006.01)

(52) U.S. Cl.
CPC .......... *C07C 303/06* (2013.01); *C07C 303/22* (2013.01); *C09B 11/18* (2013.01)

(58) Field of Classification Search
CPC ...... C07C 303/06; C07C 303/22; C09B 11/18
See application file for complete search history.

(56) References Cited

U.S. PATENT DOCUMENTS 4,764,263 A 8/1988 Gregory et al.
4,775,451 A * 10/1988 Habermann et al. ..... C25B 3/02 204/78
5,378,403 A 1/1995 Shacklette
7,662,992 B2 2/2010 Kovi et al.
8,969,616 B2 3/2015 Kovi et al.
9,353,050 B2 5/2016 Kovi et al.
2004/0108220 A1 6/2004 Stephan et al.
2004/0163968 A1* 8/2004 Kern et al. ................ C25B 3/00 205/413
2008/0281127 A1 11/2008 Kovi et al.
2008/0293963 A1 11/2008 Kovi et al.
2010/0094044 A1 4/2010 Kovi et al.
2014/0257098 A1* 9/2014 Del Priore ........... A61B 5/4325 600/563

OTHER PUBLICATIONS

J. Electrochem. Soc. 1970, 117, 1353-1357 (Hand et al.).*
Sep. Purif. Technol. 2013, 118, 279-284 (Kanapathy et al.) (Year: 2013).*
Practical Process & Research Development, 2000, p. 117 (Anderson) (Year: 2000).*
Coord. Chem. Rev. 2015, 284, 329-350 (Medici et al.) (Year: 2015).*
J. Am. Chem. Soc. 2017, 139, 7448-7451 (Kawamata et al.) (Year: 2017).*
Ullman's Encyclopedia of Industrial Chemistry, 2012, 37, 425-478 (Gessner et al.) (Year: 2012).*
European Search Report Issued Nov. 2, 2023 ; 6 pages.
N.L. Weinberg et al.; "Electrochemical oxidation of organic compounds", Chemical Reviews, vol. 68, No. 4, Aug. 1968; pp. 449-523.
"AAS, GFAAS, ICP or ICP-MS? Which technique should I use? An elementary overview of elemental analysis", Thermo Elemental, 2001.
International Search Report issued in Application No. PCT/US2020/041749 on Oct. 7, 2020, 3 pages.
Written Opinion issued in Application No. PCT/US2020/041749 on Oct. 7, 2020, 8 pages.

* cited by examiner

*Primary Examiner* — Amy C Bonaparte
*Assistant Examiner* — Derek Rhoades
(74) *Attorney, Agent, or Firm* — CANTOR COLBURN LLP

(57) ABSTRACT

Disclosed herein is a method for the preparation of diarylmethane dyes and triarylmethane dyes, such as Isosulfan Blue, using electrochemistry. Further disclosed is Isosulfan Blue prepared from a process employing electrochemistry, compositions comprising the same, and use of the prepared Isosulfan Blue as an imaging agent.

31 Claims, No Drawings

METHOD FOR THE PREPARATION OF DIARYLMETHANE DYES AND TRIARYLMETHANE DYES INCLUDING ISOSULFAN BLUE

CROSS-REFERENCE TO RELATED APPLICATIONS

This application is a U.S. National Stage Application of PCT/US2020/041749, filed Jul. 13, 2020 and is related to, and claims the benefit of priority of, U.S. Provisional Patent Application No. 62/873,380, filed Jul. 12, 2019, the contents of which are incorporated herein by reference in their entirety for all purposes.

BACKGROUND

Isosulfan Blue (N-[4-[[4-(diethylamino)phenyl] (2,5-disulfophenyl) methylene]-2,5-cyclohexadien-1-ylidene]-N-ethylethanaminium hydroxide, inner salt, sodium salt) is a triarylmethane dye used as a synthetic visual lymphatic imaging agent. Isosulfan Blue can be injected as 1% aqueous injection solution into the periphery of a tumor site where the dye localizes to the lymphatic system. Tumor sentinel nodes stain blue, allowing for identification and subsequent surgical removal.

The structure of Isosulfan Blue is shown below.

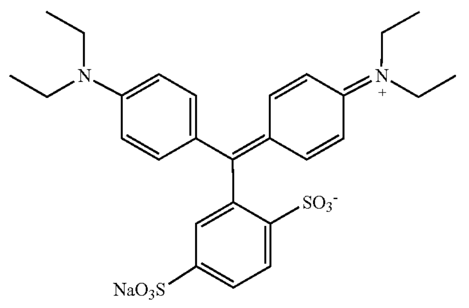

As an injectable, the purity of Isosulfan Blue is an important consideration in process development.

Known processes for the synthesis of Isosulfan Blue involve the formation of intermediate 2-[bis-(4-diethyl-amino-phenyl)-methyl]-benzene-1,4-disulfonic acid followed by chemical oxidation using reagent-based oxidants. A synthetic process as described in U.S. Pat. No. 7,662,992B2 is summarized in Scheme I.

Scheme I.

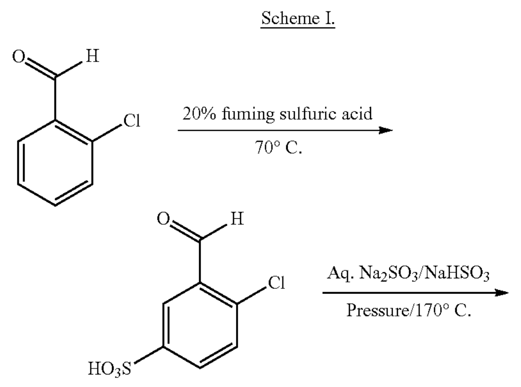

-continued

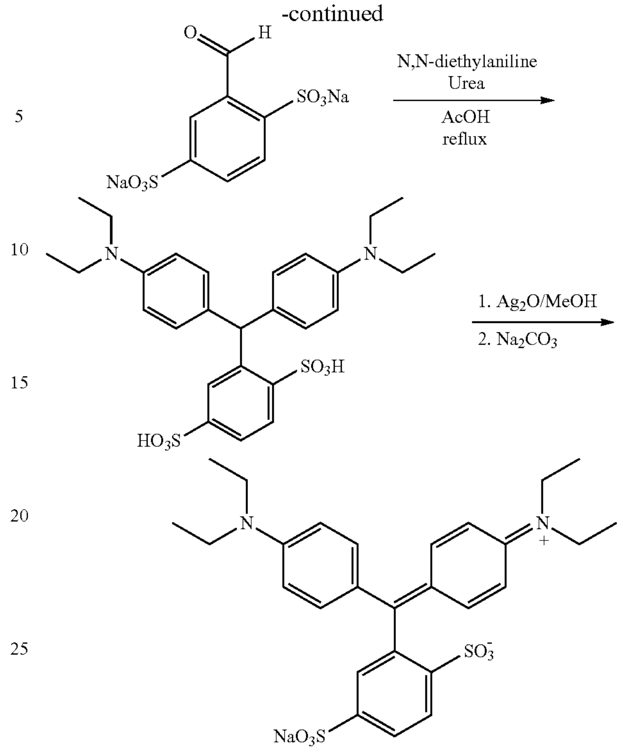

This procedure requires an expensive oxidant, silver(I) oxide. The oxidation reaction produces metallic silver that needs to be removed after use and has the further disadvantage of potentially coating reactors and processing equipment requiring costly maintenance.

There remains a need in the art for improved processes for the preparation of diarylmethane dyes and triarylmethane dyes, including Isosulfan Blue, that are facile, scalable, and allow for simplified and convenient purification of the final compound.

SUMMARY

Disclosed, in various non-limiting embodiments are process of preparing diarylmethane dyes and triarylmethane dyes, including Isosulfan Blue, using electrochemistry, diarylmethane dyes and triarylmethane dyes prepared by an electrochemical process, compositions containing the diarylmethane dyes and triarylmethane dyes prepared by an electrochemical process, and use of the synthesized dyes. Also included are highly pure diarylmethane dyes and triarylmethane dyes, specifically Isosulfan Blue.

In an embodiment, a process of preparing Isosulfan Blue comprises oxidizing 2-[bis-(4-diethylamino-phenyl)-methyl]benzene-1,4-disulfonic acid in an electrochemical process.

In another embodiment, Isosulfan Blue having one or more of the following properties:

free of metal, specifically free of a transition metal, and more specifically free of silver;

contains 0 ppm metal, more specifically 0 ppm of a transition metal, and more specifically 0 ppm silver;

contains 0 ppb metal, specifically 0 ppb of a transition metal, and more specifically 0 ppb silver;

contains a metal below the detectable limit, specifically a transition metal below the detectable limit, and more specifically silver below the detectable limit as measured by Atomic Absorption spectrometry (flame or electrothermal), Inductively Coupled Plasma (ICP), or ICP Mass Spectrometry (ICP-MS);

pure as determined by CHN analysis;

a purity as measured by HPLC that is greater than 99%, greater than 99.5%, greater than 99.8%, or greater than 99.9%;

a purity as measured by LC-MS that is greater than 95%, greater than 96%, greater than 97%, greater than 98%, greater than 99%, greater than 99.5%, or greater than 99.9%; and a purity as measured by MS/MS that is greater than 98%, greater than 99%, greater than 99.5%, or greater than 99.9%.

In a further embodiment, a process of preparing a diarylmethane dye or a triarylmethane dye, comprises oxidizing a compound of formula IIa or formula IIb in an electrochemical process:

(IIa)

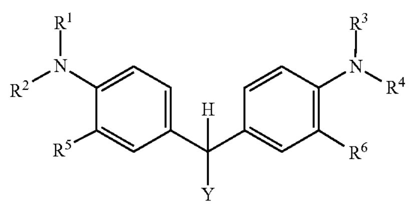

(IIb)

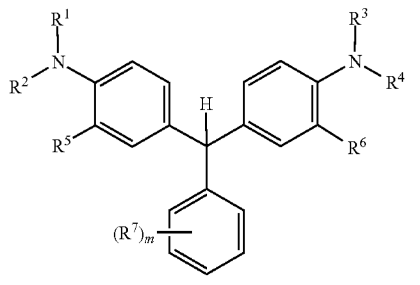

wherein each $R^1$, $R^2$, $R^3$ and $R^4$ independently is a substituted or unsubstituted $C_1$-$C_8$ alkyl, a substituted or unsubstituted phenyl, or a substituted or unsubstituted $C_1$-$C_4$ alkylphenyl, wherein the substitution can be a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl;

each $R^5$ and $R^6$ are independently hydrogen or $C_1$-$C_2$ alkyl;

Y is hydrogen, substituted or unsubstituted phenyl, or substituted or unsubstituted naphthyl;

each $R^7$ independently is a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl; and m is 1, 2, 3, or 4.

These and other features and characteristics are more particularly described below.

DETAILED DESCRIPTION

Disclosed are methods for the preparation of diarylmethane dyes and triarylmethane dyes, e.g., Isosulfan Blue, using electrochemistry (electrolysis). Electrochemistry allows for a clean and inexpensive oxidation process. The electrochemical process is flexible as an aqueous solvent or an organic solvent can be used, with aqueous solvent providing a greener approach. Furthermore, the process avoids the use of chemical oxidants, usually transition metal oxidants such as potassium permanganate, silver oxide, etc. which require the use of stoichiometric quantities that in turn produces stoichiometric quantities of often toxic transition-metal containing byproducts that need to be removed. The electrochemical method provides a clean method, as no chemical oxidants need to be added to the mixture and thus no metal-containing byproducts need to be removed after the reaction and the resulting product is metal-free.

Suitable diarylmethane dyes and triarylmethane dyes that can be prepared by the electrochemical process described herein include those compounds of formula Ia and formula Ib:

(Ia)

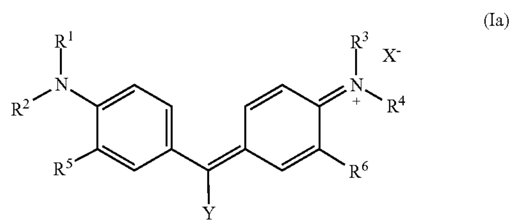

(Ib)

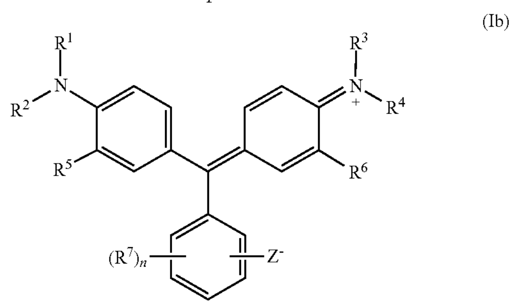

wherein each $R^1$, $R^2$, $R^3$ and $R^4$ independently is a substituted or unsubstituted $C_1$-$C_8$ alkyl, a substituted or unsubstituted phenyl, or a substituted or unsubstituted $C_1$-$C_4$ alkylphenyl, wherein the substitution can be a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl;

each $R^5$ and $R^6$ independently is hydrogen or $C_1$-$C_2$ alkyl;

Y is hydrogen, substituted or unsubstituted phenyl, or substituted or unsubstituted naphthyl;

each $R^7$ independently is a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl;

n is 0, 1, 2, or 3; and each of X and Z is an anion.

Exemplary anions for X include fluoride, chloride, bromide, iodide, hydrogensulfate, sulfate, tetrafluoroborate, formate, acetate, propionate, mono-, di- or trichloroacetate, lactate, methoxyacetate, citrate, succinate, methylsulfonate, benzenesulfonate and 2- or 4-methylbenzenesulfonate. An exemplary anion for Z is sulfonate.

When Y is substituted phenyl or substituted naphthyl, there can be 1, 2, or 3 substituents, each substituent independently is a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl.

When the dye compounds of formula Ia or formula Ib have one or more hydroxysulfonyl groups, they can be in the salt form, with a suitable counter-ion, e.g. a metal or an ammonium ion. Suitable metal ions can be an alkali metal ion such as lithium, sodium or potassium ions. Suitable ammonium ions include substituted or unsubstituted ammonium cations. Substituted ammonium cations are for example monoalkyl-, dialkyl-, trialkyl-, tetraalkyl- or benzyltrialkylammonium cations or cations derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. In an embodiment, the ion can be sodium, a substituted ammonium cation, or a combination thereof.

In an embodiment, the triarylmethane dye is Isosulfan Blue. As used herein "Isosulfan Blue," "Isosulfan Blue sodium salt," and "sodium 2-((4-(diethylamino)phenyl)(4-(diethyliminio)cyclohexa-2,5-dienylidene)methyl)benzene-1,4-disulfonate" mean the same and are used interchangeably.

The diarylmethane dyes and triarylmethane dyes can be prepared by the electrochemical oxidation of the corresponding leuco compound. Exemplary compounds include those of formula IIa and formula IIb:

(IIa)

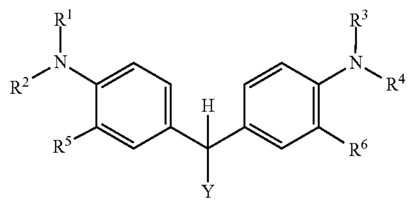

(IIb)

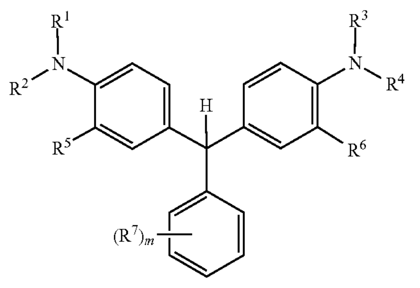

wherein $R^1$, $R^2$, $R^3$, $R^4$, $R^5$, $R^6$, $R^7$, and Y are each as previously defined, m is 1, 2, 3, or 4. In an embodiment, at least one $R^7$ is hydroxysulfonyl.

The electrochemical oxidation can be accomplished in an electrochemical cell by subjecting the leuco compound to an electrical energy in the presence of an electrolyte or a base that forms a salt in situ. The process is described below using 2-[bis-(4-diethylamino-phenyl)-methyl]-benzene-1,4-disulfonic acid as an exemplary compound used in the preparation of Isosulfan Blue. Procedures described below for the preparation of Isosulfan Blue can also be used for the electrochemical oxidation of compounds of formula IIa and formula IIb to form diarylmethane dyes and triarylmethane dyes of formula Ia and formula Ib.

It has been found that Isosulfan Blue can be prepared facilely, inexpensively, and in high purity using an electrochemical reaction to oxidize 2-[bis-(4-diethylamino-phenyl)-methyl]-benzene-1,4-disulfonic acid i to the desired product. Attempts to prepare Isosulfan Blue via oxidation of 2-[bis-(4-diethylamino-phenyl)-methyl]-benzene-1,4-disulfonic acid using organic- and peroxide reagent-based oxidants (e.g., chloranil, TEMPO, benzoyl peroxide, di-t-butyl peroxide, etc.) were not successful or prepared in suitable quantity or purity. In contrast, using electrochemical oxidation afforded the product cleanly.

The electrochemical oxidation can be accomplished in an electrochemical cell by subjecting 2-[bis-(4-diethylamino-phenyl)-methyl]benzene-1,4-disulfonic acid to an electrical energy, which includes a direct electric current, in the presence of an electrolyte or a base that forms a salt in situ. The process may be conducted in a batch or continuous type operation. In general when a batch type operation is employed in an undivided cell, the electrolyte solution is added to a reservoir along with the compound which is to undergo electrochemical oxidation. The cell is then subjected to an electrical energy within the range described herein for a period of time from about 1 minute to about 10 hours or more in duration, specifically about 10 minutes to about 5 hours, or more specifically about 30 minutes to about 2 hours.

In general when a batch type operation is employed in a divided cell, each electrode is placed in a separate reservoir with their own electrolyte solution. The two reservoirs are connected via a semipermeable membrane or salt bridge to ensure ionic conductivity. The starting material, and resulting product when formed, are in the reservoir containing the anode electrode, away from the cathode. The cell is then subjected to an electrical energy within the range described herein for a period of time from about 1 minute to about 10 hours or more in duration, specifically about 10 minutes to about 5 hours, or more specifically about 30 minutes to about 2 hours.

A summary of a non-limiting, exemplary synthetic route to Isosulfan Blue is depicted in Scheme II, with the electrochemical oxidation provided as the last step. The final oxidation of the leuco-dye 2-[bis-(4-diethylamino-phenyl)-methyl]benzene-1,4-disulfonic acid to Isosulfan Blue is accomplished using anodic oxidation. In a general exemplary procedure, the leuco-dye is dissolved in aqueous sodium carbonate and an appropriate voltage (e.g., about 2 V) is applied using electrodes of a suitable material (e.g., platinum electrodes). After an appropriate charge has passed (e.g., a total charge equaling about 2 F or more per mole of leuco-dye), the reaction is stopped and the product is isolated. Modifications to the electrode materials, nature of the electrolyte, concentration of starting material and electrolyte, amount of charge passed, and purification of the final product can be made to increase yield, improve product purity, increase process efficiency, and the like, or a combination thereof.

Scheme II.

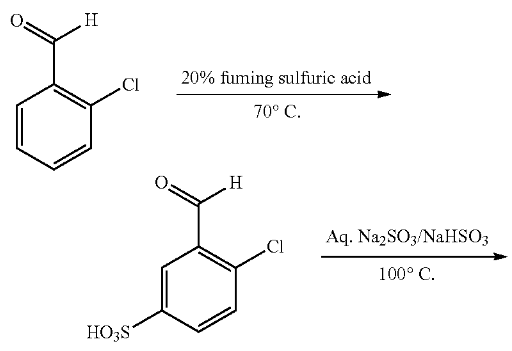

-continued

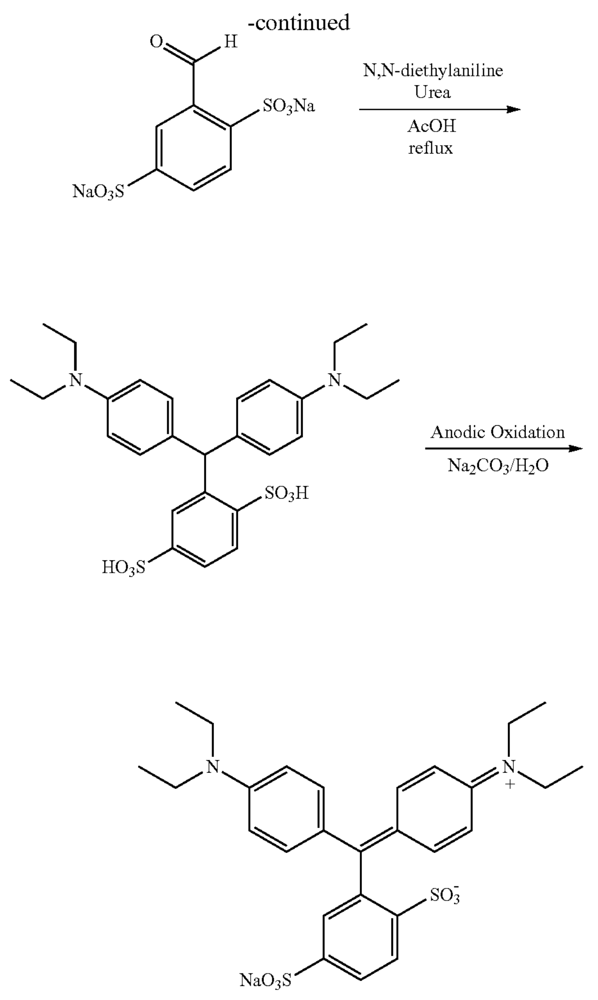

The electrochemistry can be conducted using a solvent and electrolyte or a base that forms a salt in situ where the salt functions as the electrolyte. Electrochemistry under protic conditions can employ an aqueous electrolyte solution comprising water or water and a water-miscible solvent such as a $C_1$-$C_6$ alkyl alcohol (e.g., ethanol) or alkyl ether (e.g., dioxane). The electrolyte can be an alkali or alkaline earth metal salt soluble in the reaction solution, specifically a sodium salt. Exemplary electrolytes include an alkali (e.g. sodium) or alkaline earth metal salt where the anion is carbonate, sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, perchlorate, and the like. In an alternative embodiment, the electrolyte can be formed in situ when the compound to be oxidized comprises appropriately acidic groups. For example, 2-[bis-(4-diethylamino-phenyl)-methyl]-benzene-1,4-disulfonic acid used as the starting material can be oxidized in an electrochemical process in the presence of a base. The base can include an inorganic or an organic base. Suitable inorganic bases include, for example, alkali or alkaline earth metal oxides, carbonates, and the like. In an embodiment, the base is NaOH. Suitable organic bases include amines, for example, an alkylamine (e.g. N,N-diisopropylethylamine, trimethylamine, etc.), and the like.

Electrochemistry under aprotic conditions can employ an appropriate organic solvent and suitable salts. Organic solvents include acetonitrile or a halogenated alkyl (e.g., dichloromethane) or halogenated aryl, an aryl, and the like, or a combination thereof. Suitable electrolytes for use with aprotic solvents include, for example, an alkali or alkaline earth metal salt soluble in the reaction solution, specifically sodium salts of, e.g., sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, perchlorate, and the like. As previously discussed, the electrolyte can be formed in situ using an appropriate base. For those reactions conducted in an organic solvent, an organic base can be used. Exemplary organic bases include amines, for example, an alkylamine (e.g. N,N-diisopropylethylamine, trimethylamine, etc.), and the like.

The anodic oxidation can be conducted using electrodes made from a variety of materials. Suitable anode materials include, for example, noble metals such as platinum or metal oxides such as ruthenium or chromium oxide or mixed oxides of the RuoxTiox type; graphite or carbon. Suitable cathode materials include, for example, iron, steel, stainless steel, nickel or noble metals such as platinum, graphite or carbon.

The electrolyte or base can be present in the reaction solution in a concentration of about 0.01M or greater, specifically about 0.02 to about 2 M, more specifically about 0.05 to about 1.5 M, and yet more specifically about 0.1 to about 1.0M.

The starting material can be present in the reaction solution in an initial concentration of about 0.01M or greater, specifically about 0.02 to about 2 M, more specifically about 0.05 to about 1.5 M, and yet more specifically about 0.1 to about 1.0M.

The oxidation reaction is conducted in an electrolytic cell, either an undivided cell type or divided cell type. The cell can be batch or flow. In the divided cell types the cathode and anode chambers are separated with a semiporous membrane made from materials such as, for example, sintered glass, porous porcelain, polytetrafluoroethene, polypropylene, and the like.

The electrical energy to conduct the anodic oxidation can be a voltage suitable to carry out the oxidation; for example, the voltage can be in the range of about 0.5 V up to the electrochemical window of the solvent. Suitable range includes about 1 to about 6 V, specifically about 1.5 to about 4 V. The electrical energy can be applied until a total charge equivalent to greater than 0 to about 20 F per mole of starting material passes through the reaction solution, specifically about 1 to about 12 F per mole, and more specifically about 2 to about 8 F per mole.

The temperature of the anodic oxidation can be performed over the full liquid range of the solvent. An exemplary range can be ambient temperature to about 50° C., i.e. about 17 to about 50° C. The oxidation can be conducted at or near atmospheric pressure.

After the reaction is completed, the electrolyte solution is worked up by general methods of separation. The solvent can be distilled or evaporated off, leaving the crude product. Alternatively, the product can be lyophilized or precipitated from solution using an appropriate anti-solvent. The reaction mixture may be subjected to a membrane separation to remove the electrolyte prior to isolation of the product. Such a procedure would be suitable in flow electrochemistry. The product can be further purified by crystallization, chromatography, precipitation, and the like.

Also contemplated herein are diarylmethane dyes and triarylmethane dyes, such as Isosulfan Blue, prepared using an electrochemical process. As no metal-containing oxidants are used in the preparation of the dyes, the resulting dyes are free of metal, specifically free of a transition metal, and more specifically free of silver. Determination of metal content can be made using suitable analytical techniques such as Atomic Absorption spectrometry (flame or electrothermal), Inductively Coupled Plasma (ICP), or ICP Mass Spectrometry (ICP-MS) with levels of detection in the parts per million (ppm), parts per billion (ppb), or parts per trillion (ppt). The Atomic Absorption analysis can be conducted in accordance with United States Pharmacopeia (USP)<852> ATOMIC ABSORPTION SPECTROSCOPY. In an embodiment, the dyes prepared by electrochemistry, including Isosulfan Blue, are free of metal, specifically free of a transition metal, and more specifically free of silver. The dyes prepared by electrochemistry, including Isosulfan Blue, contain 0 ppm metal, more specifically 0 ppm of a transition metal, and more specifically 0 ppm silver. The dyes prepared by electrochemistry, including Isosulfan Blue, contain 0 ppb metal, specifically 0 ppb of a transition metal, and more specifically 0 ppb silver. In an embodiment, the dyes prepared by electrochemistry, including Isosulfan Blue, contain a metal below the detectable limit, specifically a transition metal below the detectable limit, and more specifically silver below the detectable limit as measured by Atomic Absorption spectrometry (flame or electrothermal), Inductively Coupled Plasma (ICP), or ICP Mass Spectrometry (ICP-MS).

The dyes prepared by electrochemistry, including Isosulfan Blue, are pure as determined by CHN analysis, High Performance Liquid Chromatography (HPLC) analysis, Liquid chromatography-mass spectrometry (LC-MS), and Tandem Mass Spectrometry (MS/MS). The analyses can be conducted in accordance with USP <621> CHROMATOGRAPHY and USP <736> Mass Spectrometry.

In an embodiment, the dyes prepared by electrochemistry, including Isosulfan Blue, have a purity as measured by HPLC that is greater than 99%, greater than 99.5%, greater than 99.8%, or greater than 99.9%.

In an embodiment, the dyes prepared by electrochemistry, including Isosulfan Blue, have a purity as measured by LC-MS that is greater than 95%, greater than 96%, greater than 97%, greater than 98%, greater than 99%, greater than 99.5%, or greater than 99.9%.

In an embodiment, the dyes prepared by electrochemistry, including Isosulfan Blue, have a purity as measured by MS/MS that is greater than 98%, greater than 99%, greater than 99.5%, or greater than 99.9%.

Also contemplated herein are compositions and pharmaceutical compositions comprising a diarylmethane dye or triarylmethane dye, such as Isosulfan Blue, prepared using an electrochemical process. Compositions comprising Isosulfan Blue prepared using an electrochemical process can further comprise a pharmaceutically acceptable excipient. Exemplary pharmaceutically acceptable excipients include those suitable for parenteral formulations including pyrogen free water, water for injection, buffers, and the like. An exemplary composition is a 1% aqueous solution of the Isosulfan Blue prepared by electrochemistry, and optionally a phosphate buffer.

The Isosulfan Blue prepared using an electrochemical process can be used as an imaging agent, specifically in a method for sentinel lymph node mapping.

The following examples are merely illustrative of the process disclosed herein and are not intended to limit the scope hereof.

EXAMPLES

Example 1: Synthesis of Isosulfan Blue

A. Preparation of 4-Chloro-3-formyl-benzenesulfonic Acid Sodium Salt

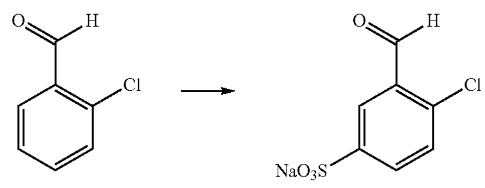

4-Chloro-3-formyl-benzenesulfonic acid sodium salt was prepared from a procedure adapted from U.S. Pat. No. 1,531,507. 20% Fuming sulfuric acid (73 mL) was added to a three neck-flask and cooled to 15-20° C. 2-Chlorobenzaldehyde (20 g, 142.3 mmol) was added dropwise while keeping the temperature of the reaction mixture below 20° C. 30 Minutes after the addition of 2-chlorobenzaldehyde was completed, the reaction mixture was heated to 70° C. and stirred overnight at 70° C. The mixture was slowly poured onto ice (300 g). Sodium chloride (150 g) was added portion-wise while stirring vigorously until a precipitate formed. The solid was filtered off, washed with diethyl ether and dried in vacuo. Yield: 30 g (87%). LC-MS: 1 peak at 1.73 min, m/z 219.83.

B. Preparation of 2-Formyl-benzene-1,4-disulfonic Acid Disodium Salt

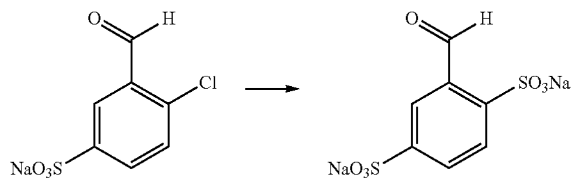

2-Formyl-benzene-1,4-disulfonic acid disodium salt was prepared from a procedure adapted from U.S. Pat. No. 1,531,507. 4-Chloro-3-formyl-benzenesulfonic acid sodium salt (5.0 g, 20.66 mmol) was dissolved in water (50 mL). Sodium sulfite (7.8 g, 62 mmol) and sodium bisulfite (645 mg, 6.2 mmol) were added and the mixture was heated at reflux overnight. The reaction mixture was cooled to room temperature and poured into 200 mL methanol. The precipitate was filtered off and washed with methanol. The filtrate was collected and the solvent was evaporated to afford 2-Formyl-benzene-1,4-disulfonic acid disodium salt. Yield: 4.3 g (67%). LC-MS: broad peak starting at 1.80 min, m/z 266.03.

C. Preparation of 2-[Bis-(4-diethylamino-phenyl)-methyl]-benzene-1,4-disulfonic Acid

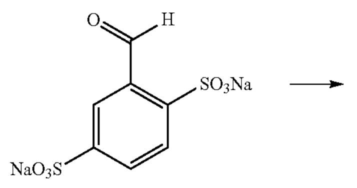

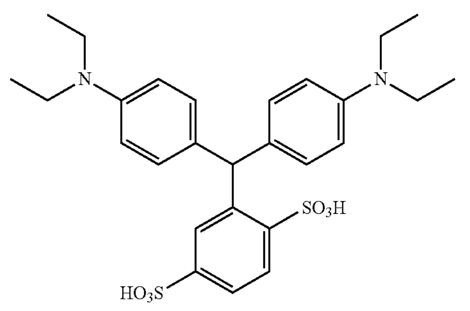

2-[Bis-(4-diethylamino-phenyl)-methyl]-benzene-1,4-disulfonic acid was prepared from procedures adapted from U.S. Pat. Nos. 2,726,252 and 4,330,476. 2-Formyl-benzene-1,4-disulfonic acid disodium salt (2.4 g, 7.87 mmol), urea (355 mg, 5.90 mmol) and N,N-diethylaniline (2.58 g, 17.32 mmol) were dissolved in acetic acid (40 mL). The mixture was stirred at reflux overnight. The reaction mixture was cooled to room temperature and poured into methanol (40 mL). The precipitate was filtered off and washed with methanol and diethyl ether. Yield: 1.98 g (46%). LC-MS: 1 peak at 1.00 min, m/z 547.19. $^1$H-NMR (300 MHz): δ (ppm) 8.12 (d, 1H, J=8.3 Hz), 7.81 (dd, 1H, J=1.8 Hz, 8.2 Hz), 7.51 (d, 1H, J=1.8 Hz), 7.47 (d, 4H, J=8.7 Hz), 7.36 (d, 4H, J=8.6 Hz), 6.88 (s, 1H), 3.63 (q, 8H, J=7.1 Hz), 1.10 (t, 12H, J=7.2 Hz).

D. Preparation of Isosulfan Blue Sodium Salt

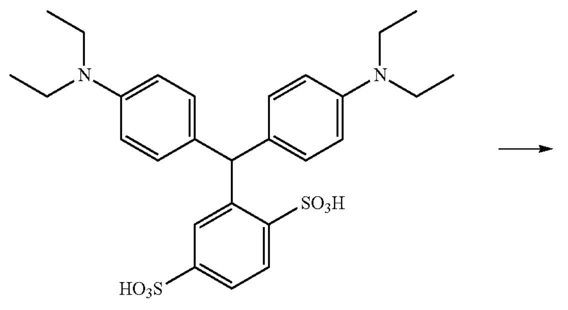

-continued

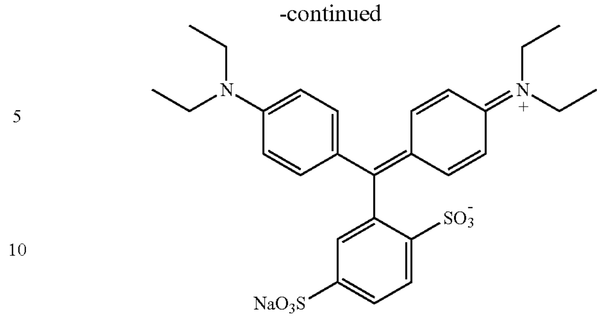

sodium 2-((4-(diethylamino)phenyl)(4-(diethylimino)cyclohexa-2,5-dienylidene)methyl)benzene-1,4-disulfonate 2-[Bis-(4-diethylamino-phenyl)-methyl]benzene-1,4-disulfonic acid (273 mg, 0.5 mmol) and sodium carbonate (159 mg, 1.5 mmol) were dissolved in water (5 mL) in an IKA ElectraSyn device, 5 mL vial. A voltage of 2V was applied over platinum electrodes, until a total charge equivalent to 2 F per mole of starting material had passed through the solution. The solvent was evaporated, and the crude mixture was adsorbed on silica gel. The product was purified by flash column chromatography using methanol in dichloromethane as the eluent. Two fractions were obtained. The first fraction contained the desired Isosulfan Blue sodium salt, the second fraction contained the disodium salt of the starting material and a small amount of Isosulfan Blue sodium salt. Yields: Isosulfan Blue sodium salt 140 mg (49%), recovered starting material (disodium salt) 113 mg (38%). LC-MS: 1 peak at 2.58 min, m/z 545.18. $^1$H-NMR (300 MHz) δ (ppm) 8.20 (d, 1H, J=8.3 Hz), 8.12 (dd, 1H, J=1.8 Hz, 8.3 Hz), 7.62 (d, 1H, J=1.7 Hz), 7.23 (d, 4H, J=9.3 Hz), 6.77 (d, 4H, J=9.4 Hz), 3.52 (q, 8H, J=7.0 Hz), 1.14 (t, 12H, J=7.1 Hz). ICP-MS: Ag<1 ppm.

Example 2: Preparation of Isosulfan Blue Sodium Salt in Flow Using Graphite Anode and Nickel Cathode 2-[Bis-(4-diethylamino-phenyl)-methyl]-benzene-1,4-disulfonic acid (17.5 g, 32 mmol) and sodium carbonate (6.78 g, 64 mmol) were dissolved in water (160 mL). The mixture was filtered and passed through a continuous flow electrolysis cell (IKA ElectraSyn Flow, graphite anode, nickel cathode, 1 mm spacer between the electrodes, total cell volume 1.2 mL) at a rate of 1.21 mL/min. A constant current of 0.98 A (corresponding to a charge of 2.5 F/mol) was passed through the cell. A fraction was collected for 60 minutes (73 mL), the solvent was evaporated, and the crude mixture was adsorbed on silica gel. The product was purified by flash column chromatography using a gradient from 0-40% methanol in dichloromethane. A total of 3.14 g of isosulfan blue was obtained, still containing about 7% of des-ethyl byproduct. $^1$H-NMR (300 MHz) δ (ppm) 8.19 (d, 1H, J=8.3 Hz), 8.10 (dd, 1H, J=1.7 Hz, 8.3 Hz), 7.60 (d, 1H, J=1.6 Hz), 7.20 (d, 4H, J=9.2 Hz), 6.74 (d, 4H, J=9.4 Hz), 3.49 (q, 8H, J=6.9 Hz), 1.11 (t, 12H, J=7.0 Hz).

Example 3: Preparation of Isosulfan Blue Sodium Salt in Flow Using Platinum Anode and Stainless Steel Cathode 2-[Bis-(4-diethylamino-phenyl)-methyl]-benzene-1,4-disulfonic acid (4.37 g, 8.0 mmol) and sodium carbonate (1.70 g, 16 mmol) were dissolved in water (40 mL). The mixture was filtered and passed through a continuous flow electrolysis cell (IKA ElectraSyn Flow, platinum anode, stainless steel cathode, 1 mm spacer between the electrodes, total cell volume 1.2 mL) at a rate of 1.21 mL/min. A constant current of 0.78 A (corresponding to a charge of 2.0 F/mol) was passed through the cell. 1H-NMR analysis in D20 revealed the following composition: 58% isosulfan blue sodium salt, 37% starting material (2-[Bis-(4-diethylamino-phenyl)-methyl]-benzene-1,4-disulfonic acid), and 6% desethyl byproduct. $^1$H-NMR (300 MHz) δ (ppm) 8.18 (d, 1H, J=8.3 Hz), 8.09 (dd, 1H, J=1.5 Hz, 8.2 Hz), 7.57 (d, 1H, J=1.7 Hz), 7.20 (d, 4H, J=9.3 Hz), 6.74 (d, 4H, J=9.4 Hz), 3.48 (q, 8H, J=7.0 Hz), 1.12 (t, 12H, J=7.1 Hz).

The term "alkyl", as used herein, means a branched or straight chain saturated aliphatic hydrocarbon group having the specified number of carbon atoms, generally from 1 to about 12 carbon atoms. The term $C_1$-$C_6$ alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$ alkyl, $C_1$-$C_4$ alkyl, and $C_1$-$C_2$ alkyl. When $C_0$-$C_n$ alkyl is used herein in conjunction with another group, for example, (phenyl)$C_0$-$C_4$ alkyl, the indicated group, in this case phenyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined herein attached through an oxygen bridge (oxygen of an alcohol radical).

"Halo" or "halogen" is any of fluoro, chloro, bromo, and iodo.

Included are the following aspects:

Aspect 1. A process of preparing Isosulfan Blue, comprising:

oxidizing 2-[bis-(4-diethylamino-phenyl)-methyl]-benzene-1,4-disulfonic acid in an electrochemical process.

Aspect 2. The process of Aspect 1, wherein the electrochemical reaction is conducted in an electrochemical cell comprising a reaction solution and electrodes, the reaction solution comprises 2-[bis-(4-diethylamino-phenyl)-methyl]-benzene-1,4-disulfonic acid, a solvent, and an electrolyte or a base, wherein the base is an inorganic or organic base.

Aspect 3. The process of Aspect 2, wherein the 2-[bis-(4-diethylamino-phenyl)-methyl]-benzene-1,4-disulfonic acid is initially present in the reaction solution at an initial concentration of about 0.01M or greater, specifically about 0.02 to about 2 M, more specifically about 0.05 to about 1.5 M, and yet more specifically about 0.1 to about 1.0M.

Aspect 4. The process of Aspect 2 or 3, wherein the solvent is an aqueous solvent, specifically water; an organic solvent; or a combination thereof.

Aspect 5. The process of any one of Aspects 2-4, wherein the electrolyte or base is present in the reaction solution at a concentration of about 0.01M or greater, specifically about 0.02 to about 2 M, more specifically about 0.05 to about 1.5 M, and yet more specifically about 0.1 to about 1.0M.

Aspect 6. The process of any one of Aspects 2-5, wherein the electrolyte is an alkali or alkaline earth metal salt where the anion is carbonate, sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, or perchlorate;

the electrolyte is sodium carbonate;

the base is an alkali or alkaline earth metal oxide or carbonate or an amine; or the base is NaOH or N,N-diisopropylethylamine.

Aspect 7. The process of Aspect 6, wherein the electrolyte or base is present at about 2 to about 4 equivalents per equivalent of 2-[bis-(4-diethylamino-phenyl)-methyl]-benzene-1,4-disulfonic acid, specifically about 3 equivalents.

Aspect 8. The process of any one of Aspects 2-7, wherein the electrodes comprise a material that is a noble metal such as platinum, a metal oxide such as ruthenium or chromium oxide, a mixed metal oxide, graphite, carbon, iron, steel, stainless steel, nickel, or a combination thereof.

Aspect 9. The process of any one of Aspects 2-8, wherein the electrodes are platinum electrodes;

a graphite anode and a nickel cathode; or a platinum anode and a stainless steel cathode.

Aspect 10. The process of any one of Aspects 2-9, wherein a voltage is applied until a total charge equivalent greater than 0 to about 20 F per mole of 2-[bis-(4-diethyl-amino-phenyl)-methyl]-benzene-1,4-disulfonic acid has passed through the reaction solution, specifically about 1 to about 12 F per mole, and more specifically about 2 to about 8 F per mole.

Aspect 11. The process of Aspect 10, wherein the voltage is about 0.5 V up to the electrochemical window of the solvent, specifically about 1 to about 6 V, more specifically about 1.5 to about 4 V.

Aspect 12. The process of any one of the preceding Aspects, wherein crude Isosulfan Blue is isolated from a reaction mixture and optionally purified to Isosulfan Blue.

Aspect 13. The process of any one of the preceding Aspects, wherein 2-[bis-(4-diethylamino-phenyl)-methyl]-benzene-1,4-disulfonic acid is prepared by reacting formyl-benzene-1,4-disulfonic acid disodium salt, urea, and N,N-diethylaniline.

Aspect 14. The process of Aspect 13, wherein 2-formyl-benzene-1,4-disulfonic acid disodium salt is prepared by reacting 4-chloro-3-formyl-benzenesulfonic acid sodium salt in the presence of sodium sulfite and sodium bisulfite.

Aspect 15. Isosulfan Blue prepared by the process of any one of the preceding Aspects.

Aspect 16. A composition comprising the Isosulfan Blue prepared by the process of any one of the preceding Aspects.

Aspect 17. Use of the Isosulfan Blue of Aspect 15, or the composition of Aspect 16, as an imaging agent.

Aspect 18. A method of imaging, comprising using the Isosulfan Blue prepared by the process of any one of Aspects 1-14 as an imaging agent.

Aspect 19. Isosulfan Blue of any one of Aspects 15-18 has one or more of the following properties:

free of metal, specifically free of a transition metal, and more specifically free of silver;

contains 0 ppm metal, more specifically 0 ppm of a transition metal, and more specifically 0 ppm silver;

contains 0 ppb metal, specifically 0 ppb of a transition metal, and more specifically 0 ppb silver;

contains a metal below the detectable limit, specifically a transition metal below the detectable limit, and more specifically silver below the detectable limit as measured by Atomic Absorption spectrometry (flame or electrothermal), Inductively Coupled Plasma (ICP), or ICP Mass Spectrometry (ICP-MS);

pure as determined by CHN analysis;

a purity as measured by HPLC that is greater than 99%, greater than 99.5%, greater than 99.8%, or greater than 99.9%;

a purity as measured by LC-MS that is greater than 95%, greater than 96%, greater than 97%, greater than 98%, greater than 99%, greater than 99.5%, or greater than 99.9%; and a purity as measured by MS/MS that is greater than 98%, greater than 99%, greater than 99.5%, or greater than 99.9%.

Aspect 20. Isosulfan Blue having one or more of the following properties:

free of metal, specifically free of a transition metal, and more specifically free of silver;

contains 0 ppm metal, more specifically 0 ppm of a transition metal, and more specifically 0 ppm silver;

contains 0 ppb metal, specifically 0 ppb of a transition metal, and more specifically 0 ppb silver;

contains a metal below the detectable limit, specifically a transition metal below the detectable limit, and more specifically silver below the detectable limit as measured by Atomic Absorption spectrometry (flame or electrothermal), Inductively Coupled Plasma (ICP), or ICP Mass Spectrometry (ICP-MS);

pure as determined by CHN analysis;

a purity as measured by HPLC that is greater than 99%, greater than 99.5%, greater than 99.8%, or greater than 99.9%;

a purity as measured by LC-MS that is greater than 95%, greater than 96%, greater than 97%, greater than 98%, greater than 99%, greater than 99.5%, or greater than 99.9%; and a purity as measured by MS/MS that is greater than 98%, greater than 99%, greater than 99.5%, or greater than 99.9%.

Aspect 21. A process of preparing a diarylmethane dye or a triarylmethane dye, comprising:

oxidizing a compound of formula IIa or formula IIb in an electrochemical process:

(IIa)

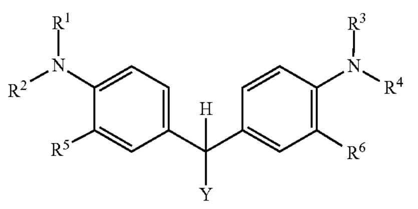

(IIb)

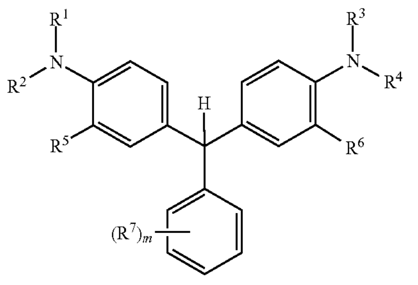

wherein each $R^1$, $R^2$, $R^3$ and $R^4$ independently is a substituted or unsubstituted $C_1$-$C_8$ alkyl, a substituted or unsubstituted phenyl, or a substituted or unsubstituted $C_1$-$C_4$ alkylphenyl, wherein the substitution can be a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl;

each $R^5$ and $R^6$ are independently hydrogen or $C_1$-$C_2$ alkyl;

Y is hydrogen, substituted or unsubstituted phenyl, or substituted or unsubstituted naphthyl;

each $R^7$ independently is a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl; and m is 1, 2, 3, or 4.

Aspect 22. The process of Aspect 21, wherein the diarylmethane dye or triarylmethane dye is a compound of formula Ia or formula Ib (Ia)

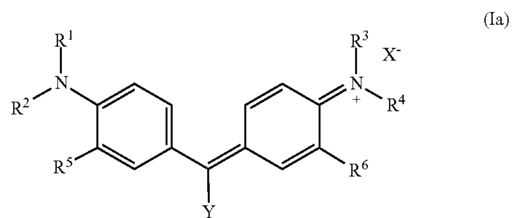

(Ib)

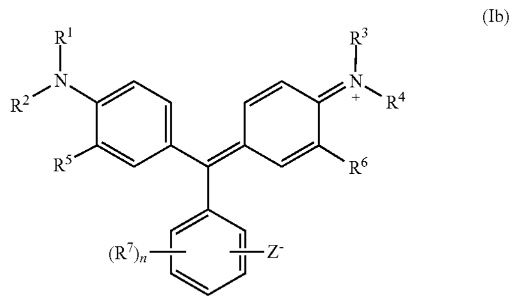

wherein $R^1$, $R^2$, $R^3$, $R^4$, $R^5$, $R^6$, $R^7$, Y, have been previously defined;

each of X and Z is an anion; and n is 0, 1, 2, or 3.

Aspect 23. The process of Aspect 22, wherein Z is sulfonate and X is fluoride, chloride, bromide, iodide, hydrogensulfate, sulfate, tetrafluoroborate, formate, acetate, propionate, mono-, di- or trichloroacetate, lactate, methoxyacetate, citrate, succinate, methylsulfonate, benzenesulfonate or 2- or 4-methylbenzenesulfonate.

Aspect 24. The process of any one of Aspects 21-23, wherein the electrochemical reaction is conducted in an electrochemical cell comprising a reaction solution and electrodes, the reaction solution comprises a compound of formula IIa or formula IIb, a solvent, and an electrolyte or a base, wherein the base is an inorganic or organic base.

Aspect 25. The process of any one of Aspects 21-24, wherein the compound of formula IIa or formula Hb is present in the reaction solution at an initial concentration of about 0.01M or greater, specifically about 0.02 to about 2 M, more specifically about 0.05 to about 1.5 M, and yet more specifically about 0.1 to about 1.0M.

Aspect 26. The process of any one of Aspects 21-25, wherein the solvent is an aqueous solvent, specifically water; an organic solvent; or a combination thereof.

Aspect 27. The process of any one of Aspects 21-26, wherein the electrolyte or base is present in the reaction solution at a concentration of about 0.01M or greater, specifically about 0.02 to about 2 M, more specifically about 0.05 to about 1.5 M, and yet more specifically about 0.1 to about 1.0M.

Aspect 28. The process of any one of Aspects 21-27, wherein the electrolyte is an alkali or alkaline earth metal salt where the anion is carbonate, sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, or perchlorate;

the electrolyte is sodium carbonate;

the base is an alkali or alkaline earth metal oxide or carbonate or an amine; or the base is NaOH or N,N-diisopropylethylamine.

Aspect 29. The process of Aspect 28, wherein the electrolyte or base is present at about 2 to about 4 equivalents per equivalent of the compound of formula IIa or formula IIb, specifically about 3 equivalents.

Aspect 30. The process of any one of Aspects 21-29, wherein the electrodes comprise a material that is a noble metal such as platinum, a metal oxide such as ruthenium or chromium oxide, a mixed metal oxide, graphite, carbon, iron, steel, stainless steel, nickel, or a combination thereof.

Aspect 31. The process of any one of Aspects 21-30, wherein the electrodes are platinum electrodes;

a graphite anode and a nickel cathode; or a platinum anode and a stainless steel cathode.

Aspect 32. The process of any one of Aspects 21-31, wherein a voltage is applied until a total charge equivalent greater than 0 to about 20 F per mole of the compound of formula IIa or formula IIb has passed through the reaction solution, specifically about 1 to about 12 F per mole, and more specifically about 2 to about 8 F per mole.

Aspect 33. The process of Aspect 32, wherein the voltage is about 0.5 V up to the electrochemical window of the solvent, specifically about 1 to about 6 V, more specifically about 1.5 to about 4 V.

Aspect 34. The process of any one of Aspects 21-33, wherein crude diarylmethane dye or triarylmethane dye is isolated from a reaction mixture and optionally purified.

Aspect 35. The process of any one of Aspects 1-14 or 21-34, wherein the electrochemical process is conducted in a continuous flow electrolysis cell.

In general, the invention may alternately comprise, consist of, or consist essentially of, any appropriate components herein disclosed. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the group(s) includes one or more groups). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process of preparing Isosulfan Blue, comprising:

oxidizing 2-[bis-(4-diethylamino-phenyl)-methyl]-benzene-1,4-disulfonic acid in an electrochemical process in the presence of an aqueous solvent, the process is conducted using electrodes wherein the electrodes are platinum electrodes; or a platinum anode and a stainless steel cathode.

2. The process of claim 1, wherein the electrochemical process is conducted in an electrochemical cell comprising a reaction solution and electrodes, the reaction solution comprises 2-[bis-(4-diethylamino-phenyl)-methyl]-benzene-1,4-disulfonic acid, the aqueous solvent, and an electrolyte or a base, wherein the base is an inorganic or organic base.

3. The process of claim 2, wherein the 2-[bis-(4-diethyl-amino-phenyl)-methyl]-benzene-1,4-disulfonic acid is initially present in the reaction solution at an initial concentration of about 0.01M or greater.

4. The process of claim 2, wherein the electrolyte or base is present in the reaction solution at a concentration of about 0.01M or greater.

5. The process of claim 2, wherein the electrolyte is an alkali or alkaline earth metal salt where the anion is carbonate, sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, or perchlorate;

the electrolyte is sodium carbonate;

the base is an alkali or alkaline earth metal oxide or carbonate or an amine; or the base is NaOH or N,N-diisopropylethylamine.

6. The process of claim 5, wherein the electrolyte or base is present at about 2 to about 4 molar equivalents per molar equivalent of 2-[bis-(4-diethylamino-phenyl)-methyl]-benzene-1,4-disulfonic acid.

7. The process of claim 2, wherein the electrodes are a platinum anode and a stainless steel cathode.

8. The process of claim 2, wherein the electrodes are platinum electrodes.

9. The process of claim 2, wherein a voltage is applied until a total charge equivalent greater than 0 to about 20 F (faraday) per mole of 2-[bis-(4-diethylamino-phenyl)-methyl]-benzene-1,4-disulfonic acid has passed through the reaction solution.

10. The process of claim 9, wherein the voltage is about 0.5 V up to the electrochemical window of the solvent.

11. The process of claim 1, wherein crude Isosulfan Blue is isolated from a reaction mixture and optionally purified to Isosulfan Blue.

12. The process of claim 1, wherein 2-[bis-(4-diethyl-amino-phenyl)-methyl]-benzene-1,4-disulfonic acid is prepared by reacting 2-formyl-benzene-1,4-disulfonic acid disodium salt, urea, and N,N-diethylaniline.

13. The process of claim 12, wherein 2-formyl-benzene-1,4-disulfonic acid disodium salt is prepared by reacting 4-chloro-3-formyl-benzenesulfonic acid sodium salt in the presence of sodium sulfite and sodium bisulfite.

14. Isosulfan Blue prepared by the process of claim 1 having a purity as measured by LC-MS that is greater than 95% and contains silver below the detectable limit as measured by Inductively Coupled Plasma Mass Spectrometry (ICP-MS), and optionally one or more of the following properties:

contains a metal below the detectable limit as measured by Atomic Absorption spectrometry (flame or electro-thermal), Inductively Coupled Plasma (ICP), or ICP Mass Spectrometry (ICP-MS);

a purity as measured by HPLC that is greater than 99%; and a purity as measured by MS/MS that is greater than 98%.

15. A composition comprising the Isosulfan Blue of claim 14.

16. Isosulfan Blue having a purity as measured by LC-MS that is greater than 95% and contains silver below the detectable limit as measured by Inductively Coupled Plasma Mass Spectrometry (ICP-MS), and optionally one or more of the following properties:

contains a metal below the detectable limit as measured by Atomic Absorption spectrometry (flame or electro-thermal), Inductively Coupled Plasma (ICP), or ICP Mass Spectrometry (ICP-MS);

a purity as measured by HPLC that is greater than 99%; and a purity as measured by MS/MS that is greater than 98%.

17. A method of imaging, comprising injecting into a periphery of a tumor site a solution comprising the Isosulfan Blue of claim 16;

allowing the Isosulfan Blue to localize to a lymphatic system to stain tumor sentinel lymph nodes, allowing for identification of the tumor sentinel lymph nodes.

18. A process of preparing a diarylmethane dye or a triarylmethane dye, comprising:

oxidizing a compound of formula IIa or formula IIb in an electrochemical process in the presence of an aqueous solvent:

(IIa)

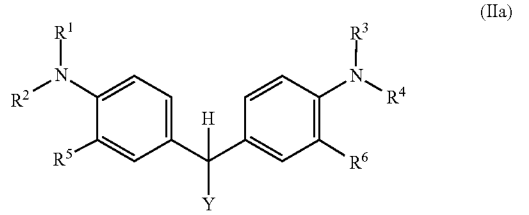

(IIb)

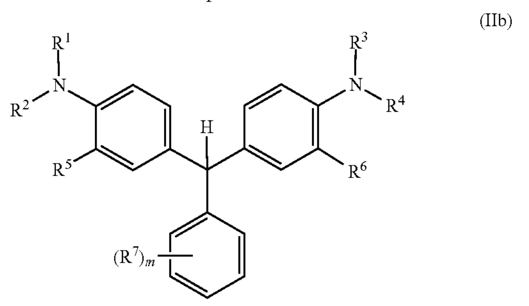

wherein each $R^1$, $R^2$, $R^3$ and $R^4$ independently is a substituted or unsubstituted $C_1$-$C_8$ alkyl, a substituted or unsubstituted phenyl, or an unsubstituted $C_1$-$C_4$ alkylphenyl, wherein the substitution can be a halogen, a $C_1$-$C_8$ alkyl, an amino, a $C_1$-$C_6$-mono- or dialkylamino, a mono- or diphenylamino, hydroxyl, $C_1$-$C_8$alkoxy, or hydroxysulfonyl;

each $R^5$ and $R^6$ are independently hydrogen or $C_1$-$C_2$ alkyl;

Y is hydrogen, substituted or unsubstituted phenyl, or substituted or unsubstituted naphthyl;

each $R^7$ independently is a halogen, a $C_1$-$C_8$ alkyl, an amino, a $C_1$-$C_6$-mono- or dialkylamino, a mono- or diphenylamino, hydroxyl, $C_1$-$C_8$ alkoxy, or hydroxysulfonyl; and m is 1, 2, 3, or 4;

the process is conducted using electrodes wherein the electrodes are platinum electrodes; or a platinum anode and a stainless steel cathode.

19. The process of claim 18, wherein the diarylmethane dye or triarylmethane dye is a compound of formula Ia or formula Ib (Ia)

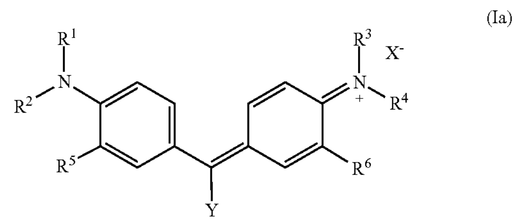

(Ib)

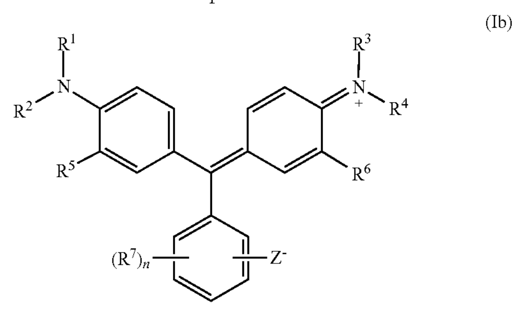

wherein $R^1$, $R^2$, $R^3$, $R^4$, $R^5$, $R^6$, $R^7$, Y, have been previously defined;

each of X and Z is an anion; and n is 0, 1, 2, or 3.

20. The process of claim 19, wherein Z is sulfonate and X is fluoride, chloride, bromide, iodide, hydrogensulfate, sulfate, tetrafluoroborate, formate, acetate, propionate, mono-, di- or trichloroacetate, lactate, methoxyacetate, citrate, succinate, methylsulfonate, benzenesulfonate or 2- or 4-methylbenzenesulfonate.

21. The process of claim 18, wherein the electrochemical process is conducted in an electrochemical cell comprising a reaction solution and electrodes, the reaction solution comprises a compound of formula IIa or formula IIb, the aqueous solvent, and an electrolyte or a base, wherein the base is an inorganic or organic base.

22. The process of claim 18, wherein the compound of formula IIa or formula IIb is present in the reaction solution at an initial concentration of about 0.01M or greater.

23. The process of claim 21, wherein the electrolyte or base is present in the reaction solution at a concentration of about 0.01M or greater.

24. The process of claim 21, wherein the electrolyte is an alkali or alkaline earth metal salt where the anion is carbonate, sulfate, hydrogen sulfate, an alkyl sulfate, an alkyl sulfonate, a halide, a phosphate, a carbonate, an alkyl phosphate, an alkyl carbonate, a nitrate, an alkoxide, tetrafluoroborate, or perchlorate;

the electrolyte is sodium carbonate;

the base is an alkali or alkaline earth metal oxide or carbonate or an amine; or the base is NaOH or N,N-diisopropylethylamine.

25. The process of claim 24, wherein the electrolyte or base is present at about 2 to about 4 molar equivalents per molar equivalent of the compound of formula IIa or formula IIb.

26. The process of claim 21, wherein the electrodes are a platinum anode and a stainless steel cathode.

27. The process of claim 21, wherein the electrodes are platinum electrodes.

28. The process of claim 18, wherein a voltage is applied until a total charge equivalent greater than 0 to about 20 F (faraday) per mole of the compound of formula IIa or formula IIb has passed through the reaction solution.

29. The process of claim 28, wherein the voltage is about 0.5 V up to the electrochemical window of the solvent.

30. The process of claim 18, wherein crude diarylmethane dye or triarylmethane dye is isolated from a reaction mixture and optionally purified.

31. The process of claim 1, wherein the electrochemical process is conducted in a continuous flow electrolysis cell.

* * * * *